United States Patent
Tanner et al.

[19]

[11] Patent Number: 5,962,696
[45] Date of Patent: Oct. 5, 1999

[54] PROCESS FOR THE PREPARATION OF 1-(N 2-(S)-ETHOXYCARBONYL)—3 PHENYLPROPYL-N6-TRIFLUORACETYL))-L-LYSYL-L-PROLIN (LISINOPRIL(TFA) ETHYLESTER, LPE))

[75] Inventors: Herbert Tanner, Hanau; Karlheinz Drauz, Freigericht; Klaus Stingl, Alzenau; Gerhard Sator, Dieburg; Horst Bethge, Rodenbach; Roland Moller, Hammersbach; Thomas Tacke, Friedrichsdorf; Claus Rehren, Aschaffenburg, all of Germany

[73] Assignee: Degussa Aktiengesellschaft, Frankfurt, Germany

[21] Appl. No.: 09/094,319

[22] Filed: Jun. 9, 1998

[51] Int. Cl.$^6$ .................................................. C07D 207/08
[52] U.S. Cl. ................................................ 548/533
[58] Field of Search ................................................ 548/533

[56] References Cited

U.S. PATENT DOCUMENTS

| | | | |
|---|---|---|---|
| 5,227,497 | 7/1993 | Inoue et al. | 548/533 |
| 5,514,401 | 5/1996 | Zeidler et al. | 426/429 |

*Primary Examiner*—Robert W. Ramsuer
*Assistant Examiner*—Dominic Keating
*Attorney, Agent, or Firm*—Omri M. Behr, Esq.

[57] ABSTRACT

There is provided a process for the work-up of this material having the formula (I)

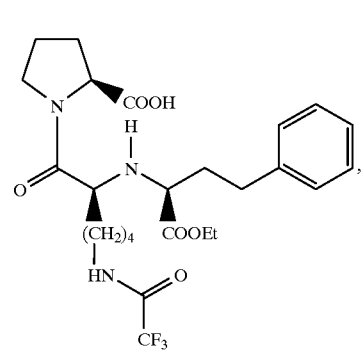

because of its poor crystallizability has heretofore been available only with large yield losses. The yield losses are due to the fact that the crystals of this compound are associated with large amounts of residual solvent material which gives rise to complex and expensive drying procedures. In accordance with the present invention the crude LPE is dried by means of fluid or supercritical carbon dioxide which maces it possible to reduce drying times from the previous range of about 124 hours to about 10 hours for the same amount of product and thus produce a dry LPE which has smaller amounts of residual solvent, as well as smaller by-products than that obtained by conventional drying.

18 Claims, 1 Drawing Sheet

PROCESS FOR THE PREPARATION OF 1-(N 2-(S)-ETHOXYCARBONYL)— 3 PHENYLPROPYL-N6-TRIFLUORACETYL))-L-LYSYL-L-PROLIN (LISINOPRIL(TFA) ETHYLESTER, LPE))

FIELD OF THE INVENTION

The invention involves a procedure for the preparation of 1-(N2-(S)-ethoxycarbonyl)-3-phenylpropyl)-N6-trifluoracetyl)-L-lysyl-L-proline (LPE, compound I).

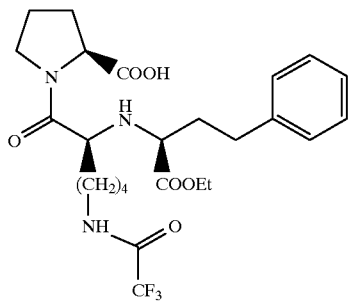

(I)

The N-substituted amino acids of this type are valuable intermediates for the manufacture of inhibitors of angiotensin converting enzymes (ACE), that function as blood pressure regulators.

Compound I is the direct precursor of 1-(N2-((S)-Carboxy)-3-phenyl-propyl))-L-lysyl-L-proline (Lisinopril II) which shows highly successful therapeutic results in the prevention of hypertension (Zestral, Coric, Prinivil).

DISCUSSION OF THE PRIOR ART

Compound I is obtained in accordance with the state of the art through reductive amination of 2-oxo-4-phenyl-butylethylester with the dipeptide Lys(Tfa)-Pro (J.Org.Chem., 1988, 53, 836–8441 describes such a procedure).

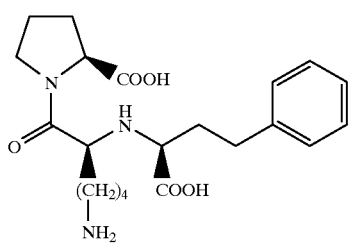

(II)

Compound I is obtained in yield of 42% through the basic extraction of the reaction solution, a re-extraction of the product into an organic solvent at pH 4.6 and subsequent crystallization from methyl-tert.butylether and cyclohexane mixture.

EP 05 23 449 discloses the synthesis of compound I which is obtained in a yield of 60% as shown in Example 3. The work-up of the crude product obtained in accordance with this procedure comprises crystallization from methyl-tert-butylether, as well as the basic and an acidic extraction step. Furthermore, other methods founded on non-reductive amination are known from EP 0 336 368 A2. However, these are less advantageous of the synthesis of compound I.

The basic extraction- an extraction of the aqueous phase product is necessary to remove the impurities from the amination reaction. However, it is always accompanied by product losses due to amide and/or ester splitting of I after II, as well as from I to compounds III and IV.

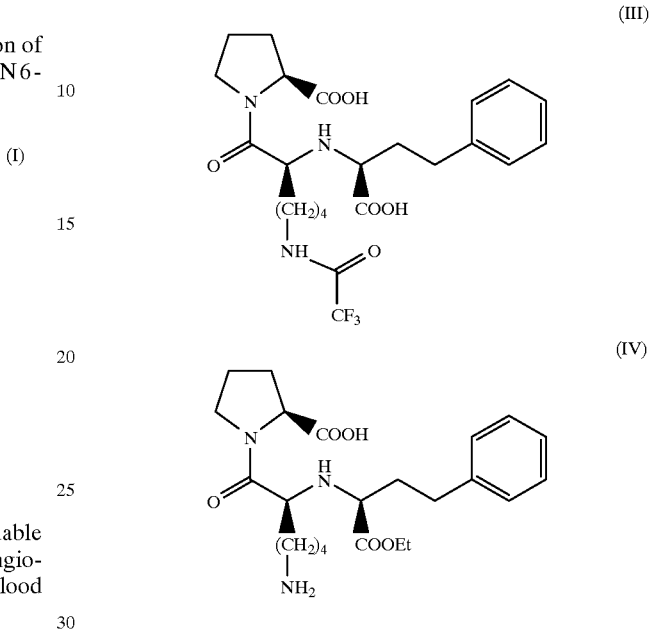

In order to minimize these product losses, one must work with precisely set pHs at low temperatures and with contact times held as short as possible. This is tedious and especially fraught with technical difficulties.

Crystallization from pure methyl-tert-butylether leads to poorly filterable granulated crystals and too often unsatisfactory yields (EP 0 645 398 A1). If one permits compound I to crystallize from solutions having higher concentration an additional recrystallization is necessary.

The addition of cyclohexane is also described (J. Org. Chem., 1988, 53, 836–844) as giving rise to increased yield during crystallization. In this procedure however, the danger of separation as an oil exists which makes the isolation of the product more difficult and not only in the technical sense.

In EP 0 645 398 A1 there is shown the possibility of crystallization of compound I from solvents or solvent mixtures. Herein it turns out that the use of methyl-tert.butylether or a methyl-tert.butylether containing mixture, results in a rather substantial solvent residue in the crystals after crystallization. In fact, the solvent material is bound into the crystal. This LPE raw material is extremely difficult to dry. Long drying times can negatively influence product quality (i.e., the formation of diketopiperazine (DKP) at elevated temperatures), and a tendency to charring make specially costly drying concepts necessary.

A work-up procedure in WO 95/07928 describes extraction with subsequent crystallization. In this procedure the raw material from the LPE formation is worked up by a plurality of fluid/fluid extraction steps at pH between 0 and 6.3 before it is crystallized from a mixture of methyl-tert.butylether and methylcyclohexane at reduced temperatures. This procedure as well as that described above, gives rise to a product with a very high proportion of the solvent. The difficulties associated with isolation and drying as set forth above apply equally to the thus obtained LPE itself. The disadvantage of the known procedures is that a practical work-up is difficult to achieve which runs counter to an economically feasible manufacture of compound I.

LPE (I) because of DKP formation, is sensitive to desethylation and desacetylation. Thus, only very mild conditions can be applied to this work-up, in fact only a very mild conditions of temperature, pH, etc. can be utilized in this drying step. The crystallization as it is described in the state of the art, is only operative with very few solvents or solvent mixtures and the thus obtained crystals always have a very high residual dampness, that is to say, the solvents are bound into the crystals which requires exceedingly long drying procedures under very mild conditions.

The very long drying times coupled with high residual moisture of the raw materials impact not only on purity of LPE end product but to the by-product spectrum and the properties of the sample with respect to charring and stickiness as well as solvent residue content, all of which have a negative impact.

SUMMARY OF THE INVENTION

The task of the present invention therefore is to provide an improved procedure for the work-up of raw material obtained in the LPE production process in such a manner that the conventional long and LPE stressing drying times can be reduced. It is furthermore the task of the invention to provide an LPE end product by this new procedure which is particularly pure with respect to residual solvent content, by-product spectrum and product qualities with respect to charring and stickiness. This and further named tasks are solved by a procedure work-up of crude material of an LPE production process comprising enriched LPE material is treated with fluid or supercritical $CO_2$.

Advantageous modifications in the procedures of the present invention are the subject of the subclaims dependent upon claim 1.

Because the raw material of an LPE production process in which enriched LPE is present is treated with liquid or supercritical $CO_2$, one is able to advantageously achieve a reduction of the drying time from the previously unsatisfactory (one week per batch to 10 hours per bath), accompanied by the provision of a high quality product.

This unforeseeable improvement in the work-up process is basic for the development of an economically interesting procedure for the previously mentioned anti-hypertensive material of formula (I). The raw material of the LPE production process to be worked up can be obtained from a reaction mixture of a final reaction step, which is partially or totally freed of solvent, or one obtained from conventional extraction and/or crystallization of a precleaned LPE charge, in which the LPE is at least enriched.

The treatment of this material with fluid or supercritical $CO_2$ can preferably occur through extraction or crystallization with the solvent. With respect to extraction of a charge of fluid raw material, one may employ a fluid-fluid extraction suitably continually in so-called counter-current columns. Therefore the undesirable components of the raw material are dissolved in one liquid phase while the LPE enriches itself in the other.

It is also advantageous in addition thereto, that already solid material which has been obtained by conventional crystallization and therefore contains a very high solvent residue, is cleaned by means of solid/liquid extraction. Suitably, the impurities are preferably dissolved in the $CO_2$ as solvent, and swept through the raw material by a stream of $CO_2$. The solid material however should be held back by suitable means, whereby the desired cleaning effect occurs.

Another preferred work-up method of the process is the treatment of the raw material with fluid or super critical $CO_2$ during crystallization. In such a procedure the fluid raw material can be taken up in $CO_2$ as solvent or vice versa. This gives rise to a change in the solubility behavior of the LPEs (I) in the solution which is now formed from the original solvent of the LPE production process and the supercritical or liquid $CO_2$, whereupon crystallization takes place.

It is just as preferred however to dissolve the solid or conventionally precrystallized raw material containing the higher proportion of residual solvent in fluid or supercritical $CO_2$ or at least partially dissolve it and, through alteration of the solution qualities of the $CO_2$ for LPE (I), for example by change of pressure or temperature, to induce crystallization.

In the above-mentioned procedure, it is essential that the raw material in question be contacted with fluid or supercritical $CO_2$. This can occur batchwise or continuously wherein the $CO_2$ as a solvent for the raw material is, according to the course of the work-up, either streamed through or poured over. In continuous through-streaming the undesired by-products are dissolved in the $CO_2$ and the insoluble or poorly soluble solid LPE is held back by suitable means.

During the flowing over of the fluid or solid raw material with fluid or super critical $CO_2$, the undesired compounds are dissolved in the $CO_2$ whereas the LPE as dissolved cleaned components or solids, is separated from the $CO_2$ solvent by suitable means.

After one of the previously described process variants has been carried out, the separated $CO_2$ which is still in a fluid or supercritical condition and which is contaminated with impurities from the LPE production process, can subsequently be depressurized in an adjacent vessel of the arrangement as is described hereinbelow in the exemplification, so that the impurities are separated into this vessel either as liquids or solids. The impurities can thus be readily collected, detoxified or readily worked up again.

The now gaseous $CO_2$ is subsequently recondensed, collected in a reserve receptacle and, in the newly liquid state, can again be utilized for further work-up.

BRIEF DESCRIPTION OF THE DRAWINGS

In FIG. 1, the raw material is charged into vessel C. Fluid $CO_2$, which is held in collection container D thus streams to pump P which compresses the $CO_2$ to the extraction pressure which by means of heat exchanger E2 is warmed to the extraction temperature and is then transported into an extractor or an extraction column.

On the way through the extractor, in particular column C, the extractable materials are dissolved in the $CO_2$. The $CO_2$ containing the dissolved materials is lead to separator S. By change of pressure and/or temperature, the solubility in $CO_2$ in the separator is reduced so that the extract is precipitated there. This separation can take place in several steps so that extraction fractions of different qualities can be obtained. The gaseous $CO_2$ from separator S is liquified in a chilled condenser and captured in collection container D.

Figure 1:
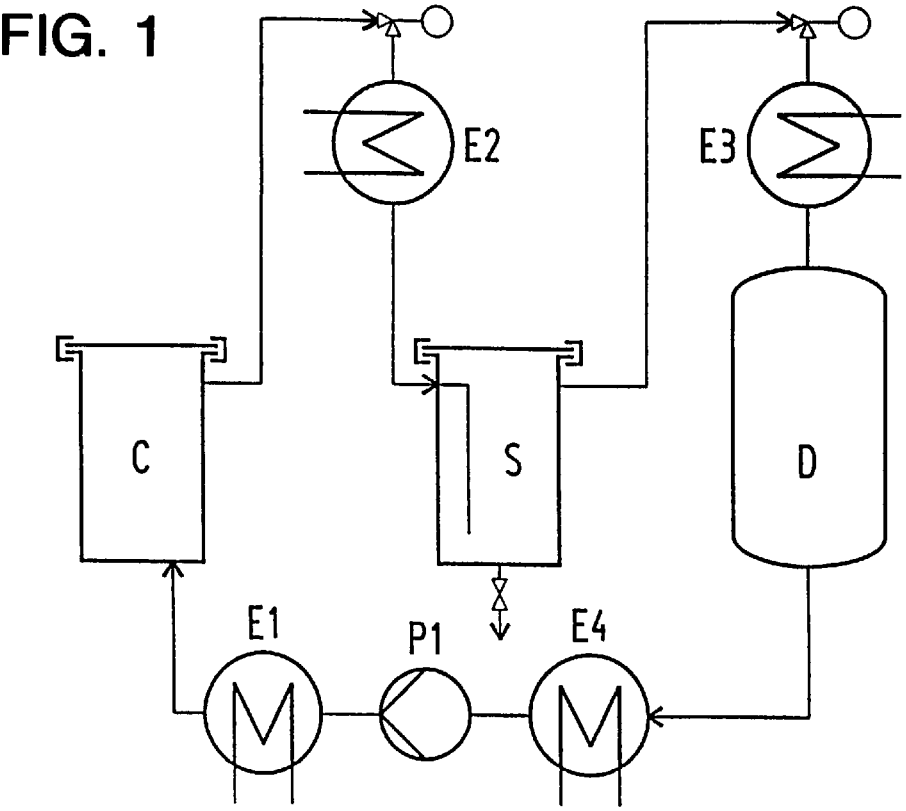
FIG. 1 shows diagrammatically suitable apparatus for carrying out the above-described drying procedure.
Figure 2:
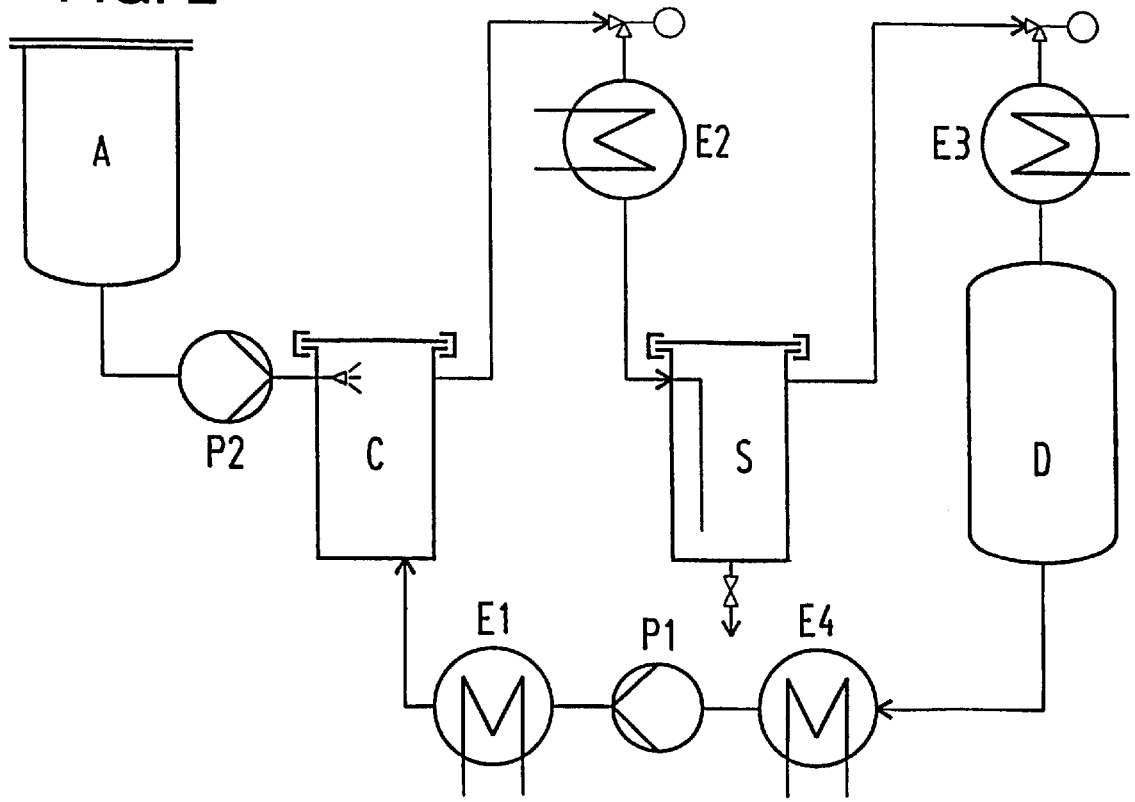
FIG. 2 show diagrammatically a crystallization apparatus.

A further arrangement for crystallization will be noted from FIG. 2. The components C, D, E1 through 4, P and S correspond to those in FIG. 1. There is additionally provided another reserve container A and a pump P2. Reserve container A comprises a solution of the raw material which, in contrast to the arrangement of FIG. 1, is continuously supplied to vessel C via pump P2. The path of $CO_2$ follows in the same manner as FIG. 1 so that a countercurrent is formed between the $CO_2$ and the solution of raw material.

DESCRIPTION OF THE PREFERRED EMBODIMENTS

It is thus possible to carry out the work-up of LPE of the present invention using very small amounts of an ecologically friendly solvent in a recyclable circuit process. The above-described preferred embodiments of the work-up of raw material of the LPE production process are carried out suitably in as temperature range of 0–50° C., preferably between 15–45°, most particularly between 25–33° C. in a pressure range of between 50 bar to 500 bar, which give rise to fluid or supercritical $CO_2$.

The amount of $CO_2$ in hypercritical or fluid condition, which is streamed through or spilled around the charged raw material of the LPE production process lies between 10 and 40 kg/kg of product/hour. Particularly preferred is 5–20 kg/kg of product/hour.

The total amount of $CO_2$ which is run through or over the raw material thus depends upon the type and amount of impurity that should be removed. The amount, generally speaking, lies between 3 and 50 kg/kg of charged raw material.

Through the application of the above-described work-up variations in LPE production, it has been possible in a technical environment, to reduce the conventional work-up time from the order of about 124 hours to about 10 hours for the same quantity of material. These much shorter work-up times in the context of very mild conditions of the work-up procedure help to avoid decomposition of the LPE, leads to very high quality LPE formula I, whose solvent content lies under that of LPEs of formula I, dried in accordance with the state of art and having a comparable by-product content.

An LPE produced in accordance with the foregoing procedure contains by-product content and residual solvent content which is better than those produced by the procedures of the present state of the art.

In sum, it can be said that one has found that in contrast to the procedures of the prior art, the present work-up of LPE raw material based upon shorter procedure times, is more economical and based upon the use of $CO_2$ as a solvent, is more environmentally friendly, and furthermore because of the mild conditions, makes it possible to generate a purer LPE.

The following examples are used to exemplify preferred procedures of the present invention.

General Procedures for the Work-Up of Technically Produced LPE Raw Material by Means of $CO_2$ The following statements are directed to Examples 1 through 3.
a) The reaction vessel up to Example 3 was always filled with 3 kg of crude LPE.
b) The $CO_2$ stream flowed through the reaction vessel from bottom to top.
c) After corresponding flow-through amounts (Tables 2 through 4) samples were taken from the upper half and the lower half of the reaction vessel and the residual solvent amount was measured by NMR.
d) The reaction vessel was filled with a mixture of the LPE set forth in Table 1.

In order to carry out the drying experiments, 5 different charges of LPE from a reduction process dried by centrifugation were utilized whose initial analysis is set forth in Table 1. The utilized charges had a residual content of between 24 and 30% of solvent components methyl-tert.butyl-ether (MBE) and methylcyclohexane (MCH).

TABLE 1

Analysis Of LPE-Charges utilized

| LPE Charge Crude | LPE-DKP Wt. [%] | LPE-Desethyl Wt. [%] | dv [(SSS):(RSS)] | Residual solvent content per NMR [%] MtBE | MCH |
|---|---|---|---|---|---|
| 1 | 0.13 | <0.1 | 99.77:0.23 | 21.7 | 1.0 |
| 2 | 0.24 | 0.12 | 99.66:0.34 | 24.7 | 2.3 |
| 3 | 0.18 | <0.1 | 99.66:0.34 | 20.5 | 1.5 |
| 4 | 0.16 | <0.1 | 99.61:0.39 | 23.2 | 1.2 |
| 5 | 0.12 | <0.1 | 99.73:0.27 | 22.7 | 0.9 |
| 6 | 0.15 | <0.1 | 99.80:0.20 | 21.4 | 0.8 |

EXAMPLE 1

In the first example (see Table 2) the crude LPE charge to be extracted was streamed through by $CO_2$ at 90 bar in a temperature range of 21–26° C. After provision of flow-through amounts of 15, 30, 45 and 60 kg of $CO_2$, corresponding tests were taken and examined for residual solvent proportions by $^1$H-NMR. As will be seen from the table, the residual solvent amount drops to practically zero after through-put of 60 kg of $CO_2$. Only the MBE content is detected at an amount less than 0.1%. After reduction of pressure, the product can be removed in the form of a compressed mass which nevertheless has a small amount of stickiness in individual places. The break-up of the discharged product is carried out unproblemmatically.

TABLE 2

Extraction at 90 bar; Use of 3 kg Crude-LPE Charge

| Expt. Nr. | Temperature [° C.] | Gas flow rate [kg/h] | Pressure [bar] | Total $CO_2$-Amount [kg] | Test Location | Residual Solvent [%] per NMR | |
|---|---|---|---|---|---|---|---|
| 1 | 21–26 | 30 | 90 | 15 | Top | MtBE: | 6.5 |
|   |       |    |    |    |     | MCH:  | 0.7 |
| 1 | 21–26 | 30 | 90 | 15 | Bottom | MtBE: | 5.8 |
|   |       |    |    |    |        | MCH:  | 0.2 |
| 1 | 21–26 | 30 | 90 | 30 | Top | MtBE: | n. b. |
|   |       |    |    |    |     | MCH:  | n. b. |

TABLE 2-continued

Extraction at 90 bar; Use of 3 kg Crude-LPE Charge

| Expt. Nr. | Temperature [° C.] | Gas flow rate [kg/h] | Pressure [bar] | Total $CO_2$-Amount [kg] | Test Location | Residual Solvent [%] per NMR | |
|---|---|---|---|---|---|---|---|
| 1 | 21–26 | 30 | 90 | 30 | Bottom | MtBE: | <0.1 |
|   |       |    |    |    |        | MCH:  | <0.1 |
| 1 | 21–26 | 30 | 90 | 45 | Top    | MtBE: | 2.2 |
|   |       |    |    |    |        | MCH:  | 0.4 |
| 1 | 21–26 | 30 | 90 | 45 | Bottom | MtBE: | <0.1 |
|   |       |    |    |    |        | MCH:  | <0.1 |
| 1 | 21–26 | 30 | 90 | 60 | Top    | MtBE: | 0.2 |
|   |       |    |    |    |        | MCH:  | 0.1 |
| 1 | 21–26 | 30 | 90 | 60 | Bottom | MtBE: | <0.1 |
|   |       |    |    |    |        | MCH:  | <0.1 |

N.B.: not determined

EXAMPLE 2

In experiment 2 (see Table 3) after the through-put of 30 kg of $CO_2$, the pressure was raised from 90 bar to 150 bar. After a further through-put of 30 kg of $CO_2$ pressure was released and the product could be taken out of the cartridge as rod-formed material. It was possible to note very little stickiness in the discharged material. In contrast to Example 1, the proportions of residual solvent in the upper and lower portions of the cartridge are virtually identical.

TABLE 3

Extraction at 90–150 bar; 3 kg Crude-LPE

| Expt. Nr. | Temperature [° C.] | Gas Flow Rate [kg/h] | Pressure [bar] | Total $CO_2$- Amount [kg] | Test - location | Residual Solvent [%] per NMR | |
|---|---|---|---|---|---|---|---|
| 2 | 25–27 | 30 | 90  | 30 | Top    | MtBE: | 6.4 |
|   |       |    |     |    |        | MCH:  | 0.3 |
| 2 | 25–27 | 30 | 90  | 30 | Bottom | MtBE: | 0.15 |
|   |       |    |     |    |        | MCH:  | <0.1 |
| 2 | 25–27 | 30 | 150 | 60 | Top    | MtBE: | 0.3 |
|   |       |    |     |    |        | MCH:  | / |
| 2 | 25–27 | 30 | 150 | 60 | Bottom | MtBE: | <0.1 |
|   |       |    |     |    |        | MCH:  | <0.1 |

EXAMPLE 3

In the drying example No. 3 (Table 4) 4 kg of LPE charged, the extraction pressure was raised from 150 bar after through-put of 54 kg of $CO_2$ to 350 bar. After a total through-put of 80 kg of $CO_2$ the pressure was released. In this LPE material, in contrast to the previous Examples 1 and 2, no sticking locations could be found anymore. Furthermore, this dried LPE could be broken up more readily than the previous generated fractions and had no small channels or sticky locations in the discharged material.

TABLE 4

Extraction at 150–350 bar; Use of 4 kg Crude-LPE Charge

| Expt Nr. | Temperature [° C.] | Gas rate [kg/h] | Pressure [bar] | Total $CO_2$- Amount [kg] | Test - location | Residual Solvent [%] per NMR | |
|---|---|---|---|---|---|---|---|
| 4 | 27    | 30 to 10 kg $CO_2$, Then 40 | 150 | 54 | Top    | MtBE: | 0.6 |
|   |       |                              |     |    |        | MCH:  | 0.1 |
| 4 | 23–28 | 40                           | 150 | 54 | Bottom | MtBE: | Trace |
|   |       |                              |     |    |        | MCH:  | / |

TABLE 4-continued

Extraction at 150–350 bar; Use of 4 kg Crude-LPE Charge

| Expt Nr. | Temperature [° C.] | Gas rate [kg/h] | Pressure [bar] | Total $CO_2$- Amount [kg] | Test - location | Residual Solvent [%] per NMR | |
|---|---|---|---|---|---|---|---|
| 4 | 23–28 | 40 | 350 | 80 | Top | MtBE: MCH: Trace | 0.2 |
| 4 | 23–28 | 40 | 350 | 80 | Bottom | MtBE: Trace MCH: | / |

EXAMPLE 4
Comparative Experiments

A centrifuge dried crude LPE charge was dried as follows. LPE damp crude (about 25–30%) was dried in a contact dryer for 124 hours at a maximum temperature of 45° C. Afterwards, a representative sample had the following residual content.

TABLE 5

| Methylcyclohexane | <0.1 % w/w |
|---|---|
| Methyl-tert.-butylether | 0.5 % w/w |

We claim:

1. Process for the work up of LPE where the crude product obtained in an LPE production process which comprises enriched LPE material, is contacted with liquid $CO_2$ or supercritical $CO_2$.

2. The process according to claim 1, comprising extracting said enriched LPE with liquid $CO_2$ or supercritical $CO_2$.

3. The process according to claim 1, comprising crystallizing said enriched LPE with liquid $CO_2$ or supercritical $CO_2$.

4. The process in accordance with claim 2, wherein the enriched LPE is continually extracted in a liquid/liquid system.

5. The process in accordance with claim 4, wherein the extraction is carried out in a counter-current column.

6. The process in accordance with claim 2, wherein the enriched LPE is cleaned by solid/liquid extraction.

7. The process in accordance with claim 3, wherein solid enriched LPE is crystallized.

8. The process in accordance with claim 3, wherein dissolved enriched LPE is crystallized.

9. The process in accordance with claim 1, wherein liquid or supercritical $CO_2$ is streamed through or around the said enriched LPE material.

10. The process in accordance with claim 8, comprising the sequential steps of a) stream liquid $CO_2$ or supercritical $CO_2$ through or around the enriched LPE material;

b) decompressing said $CO_2$; and c) collecting the impurities from the enriched LPE carried therewith in a capture container.

11. The process according to claim 10, wherein the decompressed $CO_2$ is subsequently again compressed and again made ready for work-up.

12. The process according to claim 3, wherein the crystallization is carried out from a solvent mixture which comprises the solvents of the production process and the supercritical $CO_2$.

13. The process according to claim 7, wherein the crystallization is carried out from a solvent mixture which comprises the solvents of the production process and the supercritical $CO_2$.

14. The process according to claim 8, wherein the crystallization is carried out from a solvent mixture which comprises the solvents of the production process and the supercritical $CO_2$.

15. The process in accordance with claim 1, wherein that the $CO_2$ is provided in a pressure range 50–500 bar.

16. The process in accordance with claim 1, wherein the work-up is carried out at a temperature below 45° C. and higher than 150° C.

17. The process in accordance with claim 1, wherein the rate of through-put of $CO_2$ with respect to the enriched LPE is greater than 5 kg/kg of product and less than 20 kg/kg of product/hour.

18. The process in accordance with claim 1, wherein the $CO_2$ passing over or through the enriched LPE material is greater than 3 kg/kg of product and less than 50 kg/kg of product.

* * * * *